(12) United States Patent
Boege (10) Patent No.: US 7,248,359 B2
(45) Date of Patent: Jul. 24, 2007

(54) COMBINING MULTI-SPECTRAL LIGHT FROM SPATIALLY SEPARATED SOURCES

(75) Inventor: Steven J. Boege, San Mateo, CA (US)

(73) Assignee: Applera Corporation, Foster City, CA (US)

( * ) Notice: Subject to any disclaimer, the term of this patent is extended or adjusted under 35 U.S.C. 154(b) by 178 days.

(21) Appl. No.: 11/095,407

(22) Filed: Mar. 30, 2005

(65) Prior Publication Data

US 2006/0221336 A1    Oct. 5, 2006

(51) Int. Cl.
  *G01J 3/30*   (2006.01)
  *G01N 21/64*  (2006.01)
(52) U.S. Cl. .................. 356/317; 422/82.08; 436/172; 435/288.7
(58) Field of Classification Search ................ 356/417; 422/82.08; 435/288.7; 436/172
  See application file for complete search history.

(56) References Cited

U.S. PATENT DOCUMENTS

| | | | |
|---|---|---|---|
| 3,472,594 A * | 10/1969 | Hughes et al. | 356/320 |
| 3,532,429 A * | 10/1970 | Hughes et al. | 356/320 |
| 3,970,963 A | 7/1976 | Chester | |
| 5,528,612 A | 6/1996 | Scheps et al. | |
| 5,926,283 A | 7/1999 | Hopkins | |
| 5,982,497 A | 11/1999 | Hopkins | |
| 6,372,485 B1 | 4/2002 | Clark et al. | |
| 2002/0197734 A1 | 12/2002 | Amirkhanian | |
| 2002/0197735 A1* | 12/2002 | Amirkhanian | 436/517 |

OTHER PUBLICATIONS

Siegel, J. et al., "Whole-Field Five-Dimensional Fluorescence Microscopy Combining Lifetime and Spectral Resolution with Optical Sectioning," *Optics Letters*, Sep. 1, 2001, vol. 26, No. 17, pp. 1338-1340.
International Search Report from application No. PCT/US06/10300 dated Jan. 25, 2007, along with Written Opinion of the International Searching Authority.

* cited by examiner

Primary Examiner—F. L. Evans (57) ABSTRACT

Systems and methods for biological sample detection by combining and directing light with an optical blender that provides a composite beam from spatially and spectrally distinct non-parallel light sources.

16 Claims, 13 Drawing Sheets

COMBINING MULTI-SPECTRAL LIGHT FROM SPATIALLY SEPARATED SOURCES

FIELD

The present teachings relate to systems and methods for blending and directing light from spatially separated sources to biological samples.

BACKGROUND

Systems for detecting fluorescence can include one or more detectors to provide detection of fluorescence by each sample analyzed. These systems can include a broadband light source excitation of each sample analyzed. These systems can include filters to separate the output of the light source into multiple excitation wavelengths. It can be desirable to combine the outputs of spatially-separate and spectrally distinct light emitting diodes (LEDs) or lasers to achieve a higher flux in multispectral detection.

SUMMARY

In various embodiments, the present teachings provide for a biological sample detection system including a first light source emitting a first light beam having a first optical spectrum, a second light source spatially separated from the first light source, the second light source emitting a second light beam having a second optical spectrum, wherein the second optical spectrum is different from the first optical spectrum, and wherein the first light beam and the second light beam have non-parallel paths when entering an optical blender positioned in the paths of the first light beam and the second light beam, wherein the optical blender combines the first light beam and the second light beam into a composite beam directed toward a luminescent dye that produces emission light in relation to nucleic acid present in the biological sample, and a detector configured to detect the emission light generated in the biological sample.

In various embodiments, the present teachings provide for a method of biological sample detection including combining at least two different light beams with at least two different optical spectra coming from at least two different non-parallel light sources into a composite beam, directing the composite beam toward a luminescent dye that produces emission light in relation to nucleic acid present in the biological sample, and detecting the emission light generated in the biological sample.

Additional embodiments are set forth in part in the description that follows, and in part will be apparent from the description, or may be learned by practice of the various embodiments described herein.

BRIEF DESCRIPTION OF THE DRAWINGS

Various embodiments of the present teachings are exemplified in the accompanying drawings. The teachings are not limited to the embodiments depicted, and include equivalent structures and methods as set forth in the following description and known to those of ordinary skill in the art. In the drawings.

It is to be understood that both the foregoing general description and the following detailed description are exemplary and explanatory only and are intended to provide a further explanation of the various embodiments of the present teachings.

DESCRIPTION OF VARIOUS EMBODIMENTS

Reference will now be made to various exemplary embodiments, examples of which are illustrated in the accompanying drawings. Wherever possible, the same reference numbers are used in the drawings and the description to refer to the same or like parts.

The term "excitation light source" as used herein refers to a source of irradiance that can provide excitation that results in fluorescent emission. Light sources can include, but are not limited to, LEDs, phosphor coated LEDs, organic LEDs (OLED), phosphorescent OLEDs (PHOLED), inorganic-organic LEDs, LEDs using quantum dot technology, and LED arrays. Alternatively, the light sources can include white light, halogen lamp, lasers, solid state laser, laser diode, micro-wire laser, diode solid state lasers (DSSL), vertical-cavity surface-emitting lasers (VCSEL), thin-film electroluminescent devices (TFELD), filament lamps, arc lamps, gas lamps, and fluorescent tubes. Light sources can have high radiance, such as lasers, or low radiance, such as LEDs. Radiance refers to light emitted and can be measured in units of watts percentimeter squared per steradian. Lasers have high radiance since they emit light in substantially a single direction. LEDs have low radiance since they typically emit light into 2 pi steradians. The different types of LEDs mentioned above can have a medium to high radiance.

The term "detector" as used herein refers to any component, portion thereof, or system of components that can detect light including a charged coupled device (CCD), back-side thin-cooled CCD, front-side illuminated CCD, a CCD array, a photodiode, a photodiode array, a photomultiplier tube (PMT), a PMT array, complimentary metal-oxide semiconductor (CMOS) sensors, CMOS arrays, a charge-injection device (CID), CID arrays, etc. The detector can be adapted to relay information to a data collection device for storage, correlation, and/or manipulation of data, for example, a computer, or other signal processing system.

The term "filter" as used herein refers to any electromagnetic radiation exclusion device that can operate at a particular wavelength or range of wavelengths. Filter includes optical filters. Filter can include a shortpass filter, a longpass filter, a multi-notch filter, and/or a bandpass filter. The terms "shortpass" filter and "longpass" filter as used herein refer to relative filtering ranges on the spectrum of excitation light and emission light.

The term "sample chamber" as used herein refers to any structure that provides containment to a sample. The sample chamber can be open or transparent to provide entry to excitation light and egress to fluorescent light. The transparency can be provided by glass, plastic, fused silica, etc. The sample chamber can take any shape including a well, a tube, a vial, a cuvette, a tray, a multi-well tray, a microcard, a microslide, a capillary, an etched channel plate, a molded channel plate, an embossed channel plate, etc. The sample chamber can be part of a combination of multiple sample chambers grouped into a row, an array, an assembly, etc. Multi-chamber arrays can include 12, 24, 36, 48, 96, 192, 384, 3072, 6144, or more sample chambers. The sample chamber can be shaped to a multi-well tray under the SBS microtiter format.

The term "biological sample" as used herein refers to any biological or chemical substance, typically in an aqueous solution with luminescent dye that can produce emission light in relation to nucleic acid present in the solution. The biological sample can include one or more nucleic acid sequence to be incorporated as a reactant in polymerase chain reaction (PCR) and other reactions such as ligase chain reaction, antibody binding reaction, oligonucleotide ligations assay, and hybridization assay. The biological sample can include one or more nucleic acid sequence to be identified for DNA sequencing.

The term "luminescent dye" as used herein refers to fluorescent dyes that can be excited by excitation light or chemiluminscent dyes that can be excited chemically. Luminescent dyes can be used to provide different colors depending on the dyes used. Several dyes will be apparent to one skilled in the art of dye chemistry. One or more colors can be collected for each dye to provide identification of the dye or dyes detected. The dye can be a dye-labeled fragment of nucleotides. The dye can be a marker triggered by a fragment of nucleotides. The dye can provide identification of nucleic acid sequence in the biological sample by association, for example, bonding to or reacting with a detectable marker, for example, a respective dye and quencher pair. The respective identifiable component can be positively identified by the luminescence of the dye. The dye can be normally quenched, then can become unquenched in the presence of a particular nucleic acid sequence in the biological sample. The fluorescent dyes can be selected to exhibit respective and, for example, different, excitation and emission wavelength ranges. The luminescent dye can be measured to quantitate the amount of nucleic acid sequences in the biological sample. The luminescent dye can be detected in real-time to provide information about the identifiable nucleic acid sequences throughout the reaction. Examples of fluorescent dyes with desirable excitation and emission wavelengths can include 5-FAM™, TET™, and VIC™.

In various embodiments, the biological detection system can include at least two light sources such that the first light source can emit a first light beam having a first optical spectrum, for example, one wavelength, two wavelengths, multiple wavelengths, a range of wavelengths, etc. and the second light source can be spatially separated, such as having a different location from the first light source and a different optical spectrum. The light sources each can emit a light beam. The light beams can have non-parallel paths. Non-parallel paths can include convergent paths, divergent paths, and any path that is off parallel.

In various embodiments, the biological detection system includes a optical blender that can combine the first light beam and the second light beam into a composite beam directed toward the luminescent dye that produces emission light in relation to nucleic acid present in the biological sample. The optical blender can be positioned in the paths of the first light beam and the second light beam. The optical blender can receive the input of light beams from the light sources and can provide the output of a composite beam. The composite beam includes a complete overlap of the input light beams, a partial overlap of the input light beams, or an adjacency of the light beams such that the light paths of the contributions from each input light beam to the composite beam are substantially parallel. Adjacency, for example, can provide a composite beam where the contributions from each input light beam have paths that are side-by-side or concentric. In various embodiments, the light sources can be positioned at different modal locations of the optical blender to facilitate with the blending of the different optical spectra.

In various embodiments, the optical blender can separate the emission light into contributions of luminescent light emitted by different luminescent dyes. The detector can be configured to detect the emission light generated in the biological sample. In various embodiments, a detector can be positioned in the path of a beam separated from the emission light representing the contribution of a luminescent dye such that each dye can be detected by a specific detector. The detectors can be positioned at different modal locations of the optical blender to facilitate detection of the different optical spectra contributions separated from the emission light.

In various embodiments, the optical blender can be a grating, such as a diffraction grating, an optical prism, a beam splitter, a wedge, or a mirror array relay. In various embodiments, more than one of these optical components can be included in the detection system positioned in the path of excitation light emitted by the light sources and/or in the path of the emission light, or one positioned. In various embodiments, the optical components in the path can combine the light beam from the light sources into a composite beam and/or separate the contributions of the emission light.

In various embodiments, the optical blender can be a wedge. A wedge can be constructed out of glass or other transparent material and coated with reflective or partially reflective material. Thereby the wedge can have dichroic surfaces and reflective surfaces. The dichroic surfaces can be short pass, reflecting longer wavelengths and transmitting shorter wavelengths, or long pass, reflecting shorter wavelengths and transmitting longer wavelengths. As such, light beams of different wavelengths can have different light paths through the wedge. The different light paths can provide combination of the input beams into a composite beam. In various embodiments, the wedge can separate contributions to the emission light by operating in the reverse of combining the input beams from the light sources.

Figure 1A:
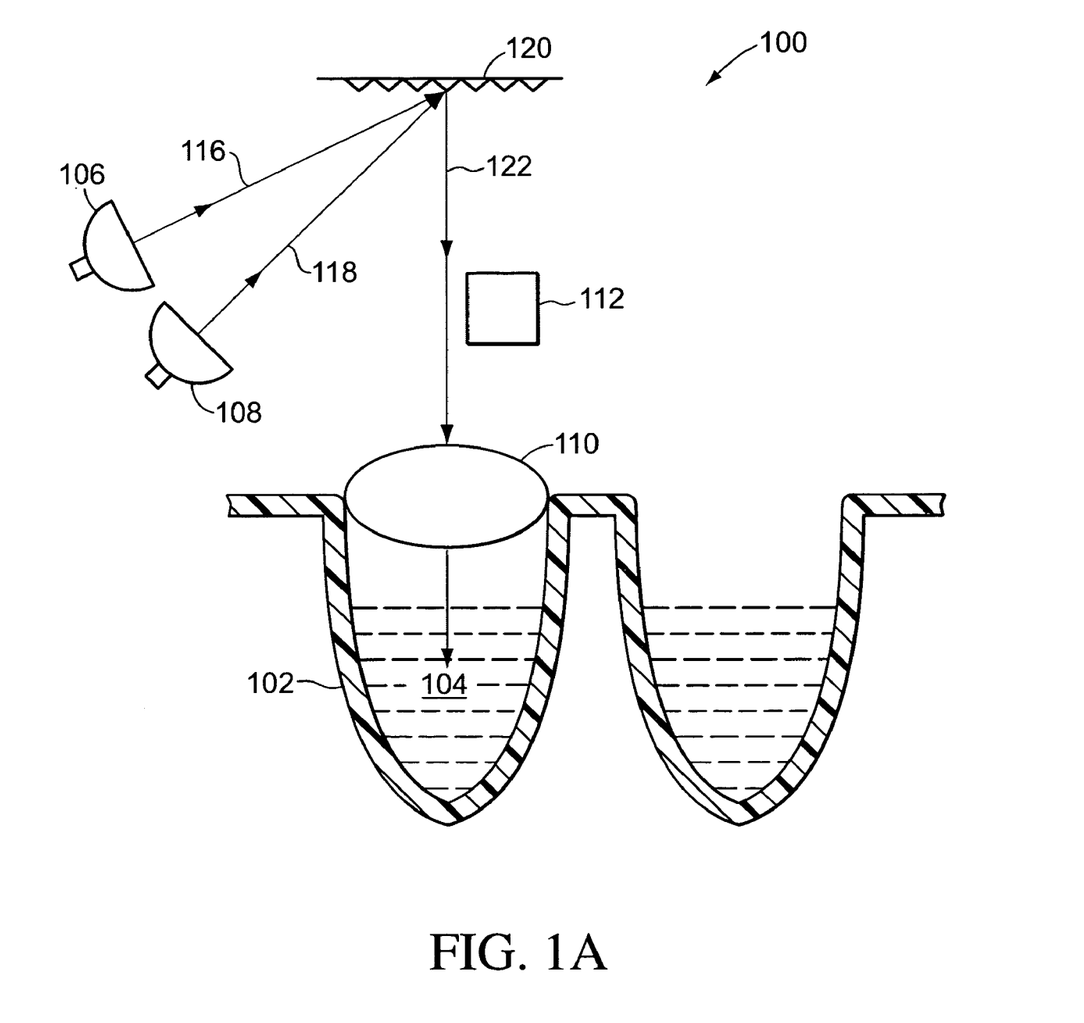
FIGS. 1A–1B and 5A–5B illustrate a side, partial cross-sectional view of a biological sample detection system including a grating according to various embodiments of the present teachings.

In various embodiments, as illustrated in FIG. 1A, a detection system 100 can include a sample chamber 102 adapted to receive a biological sample 104 containing one or more luminescent-light emitting dyes, for example, fluorescent dyes. The system 100 can include a first excitation light source 106, a second excitation light source 108, an optical assembly 110, and a detection assembly 112 for detecting luminescent light emitted from the biological sample 104.

The first and second excitation light sources 106, 108 can be spatially separated from one another. The first excitation light source 106 can be configured to provide a first beam of light 116, and the second excitation light source 108 can be configured to provide a second beam of light 118. The first and second light sources 106, 108 can provide the respective non-parallel first and second light beams 116, 118. As shown, the first and second light beams have converging paths. The first and second beams of light 116, 118 can have optical spectra that differ from one another. For example, the first and second beams of light 116, 118 can have substantially different wavelengths, such as different color LEDs or lasers.

In various embodiments, the system 100 can include an optical blender such as, for example, a diffraction grating 120. The diffraction grating 120 can be positioned in the path of the input light beams, for example, as shown substantially at the intersection of light beams 116, 118. The diffraction grating 120 can be configured to combine the light beams 116, 118 and output a composite beam 122 including optical spectra from both light beams 116, 118 directed toward a luminescent dye that produces emission light in relation to nucleic acid present in the biological sample 104. The optical assembly 110 can be between the diffraction grating 120 and the biological sample 104.

In various embodiments, the fluorescent detection system 100 can include one or more additional light sources spatially separated from the first and second light sources 106, 108. Each of the additional light sources can provide a beam of light whose optical spectrum differs from one another and/or from those of the first and second beams of light 116, 118. For example, each additional beam of light can have a substantially different wavelength from one another and/or from those of the first and second beams of light 116, 118.

In various embodiments, the luminescent detection system 100 can include two or more diffraction gratings 120, so long as the diffraction grating proximate to the biological sample can output the composite beam 122 directed along a coincident path toward the biological sample 104.

Figure 1B:
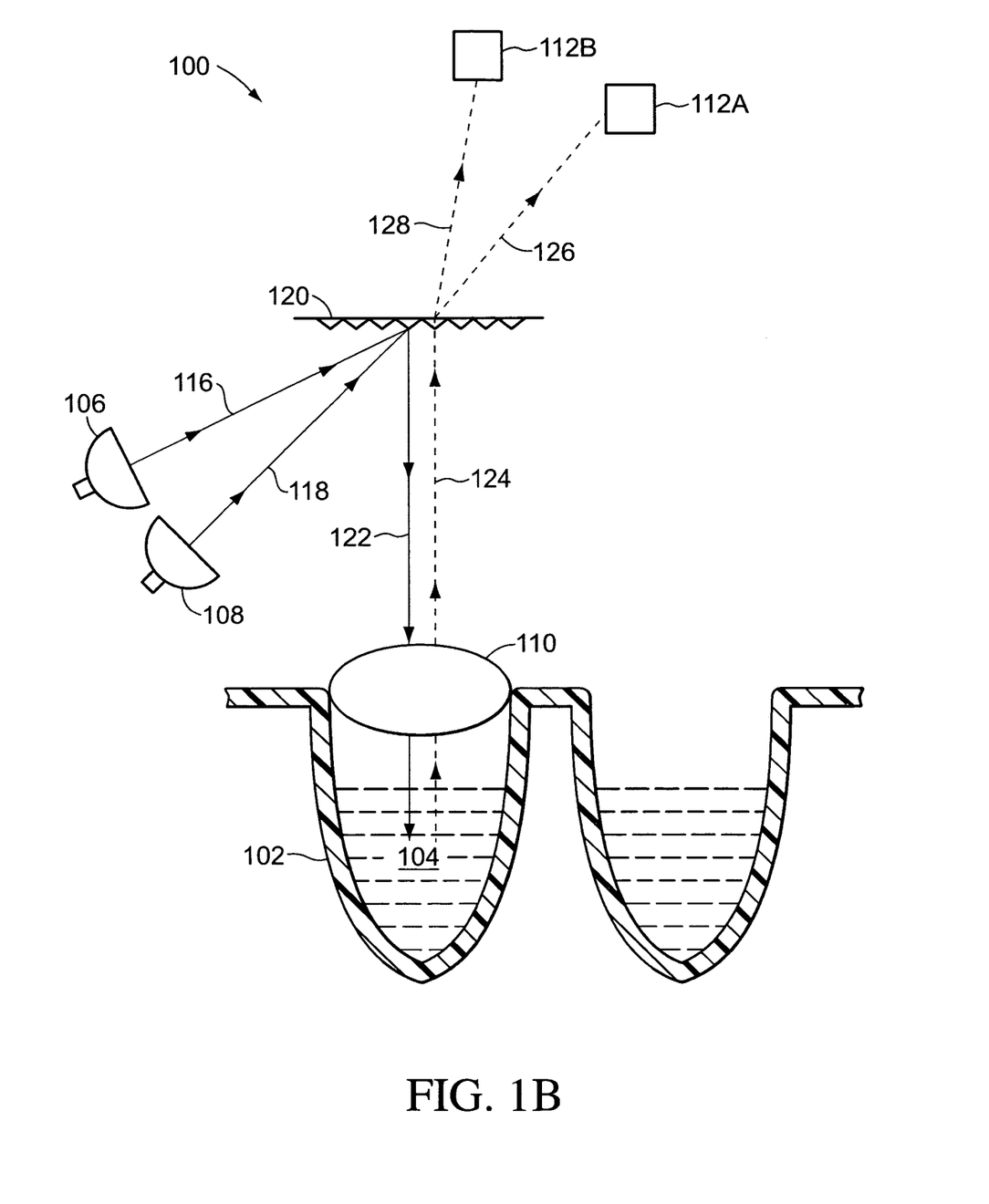

In various embodiments, as illustrated in FIG. 1B, the optical blender can be a diffraction grating 120 that can separate different contributions to the emission light 124 coming from the biological sample 104 and transmitted through the grating. The different contributions can be emitted by different luminescent dyes in the biological sample 104. The diffraction grating 120 can separate the emission light 124 into a first contribution 126 having a first optical spectrum and a second contribution 128 having a second optical spectrum different from the first optical spectrum. Detectors 112A and 112B can be positioned in the paths of first contribution 126 and second contribution 128, respectively, to detect their respective optical spectrum. Detectors 112A and 112B can be positioned in the modal locations of the diffraction grating 120.

Figure 5A:
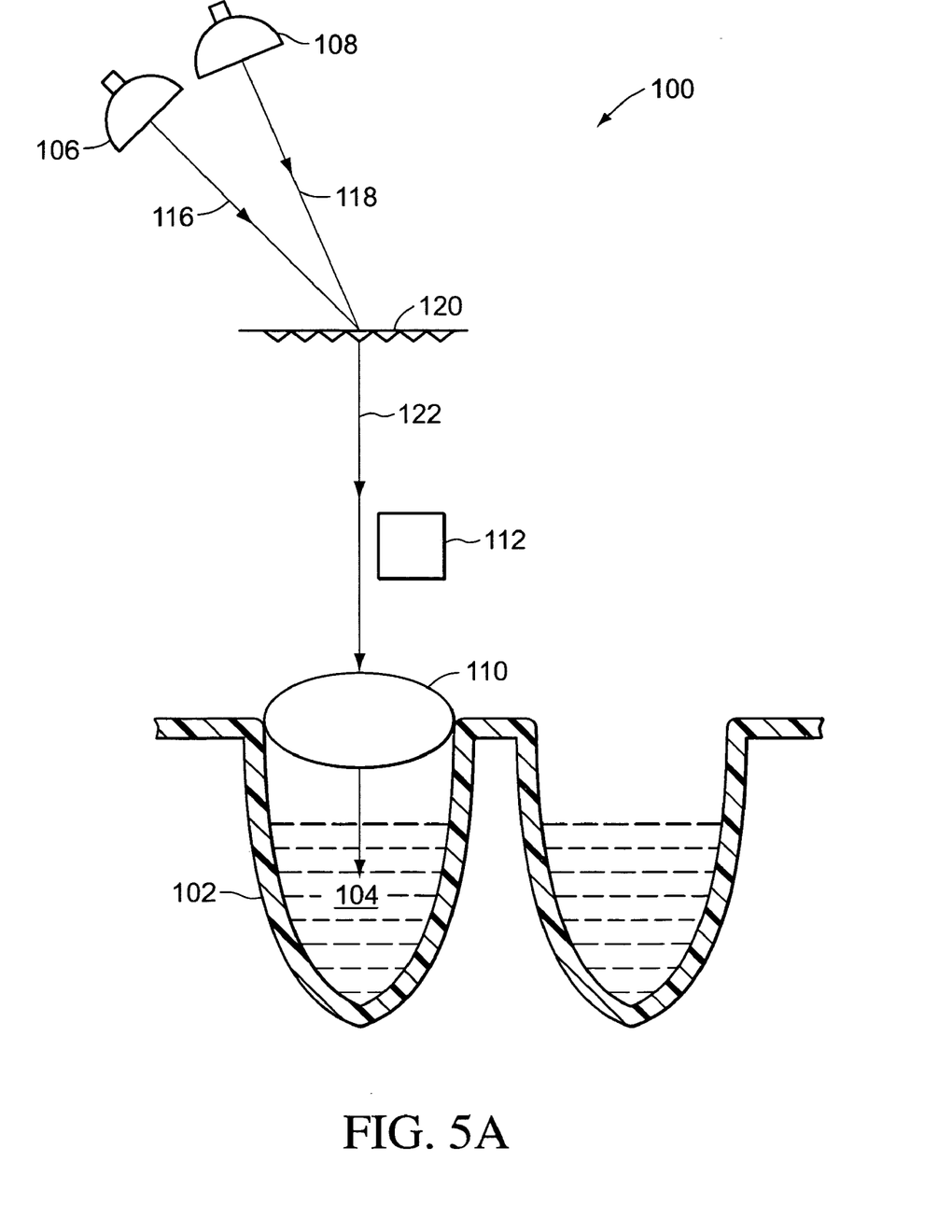
Figure 5B:
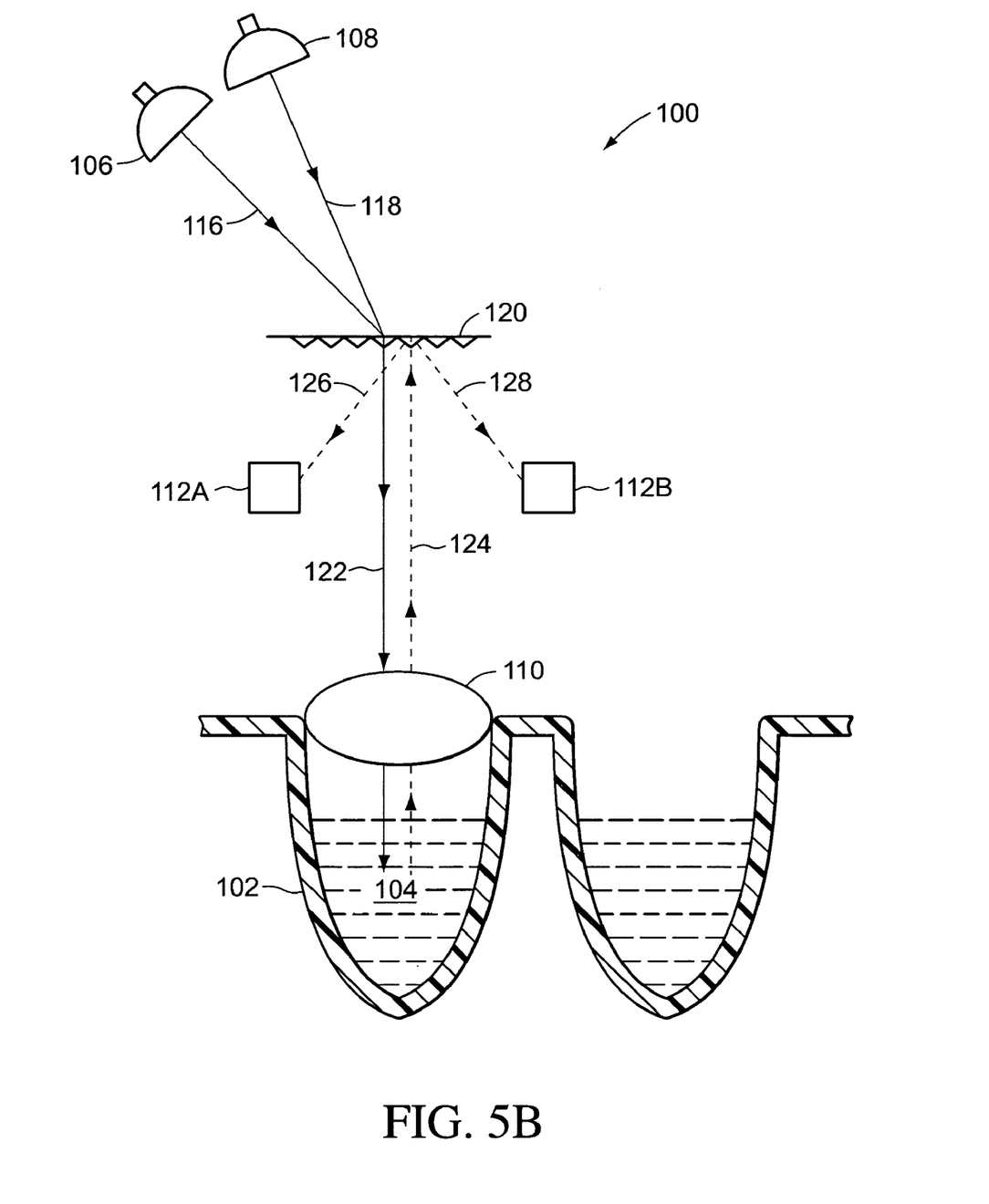

In various embodiments, as illustrated in FIGS. 5A and 5B, the optical blender can be a grating 120 that can transmit first light beam 116 and second light beam 118 to direct composite beam 122 toward the luminescent dye in the biological sample 104. As illustrated in FIG. 5B, the emission light 124 can be separated into contributions 126 and 128 as described above by being reflected and diffracted by the grating 120.

Figure 2A:
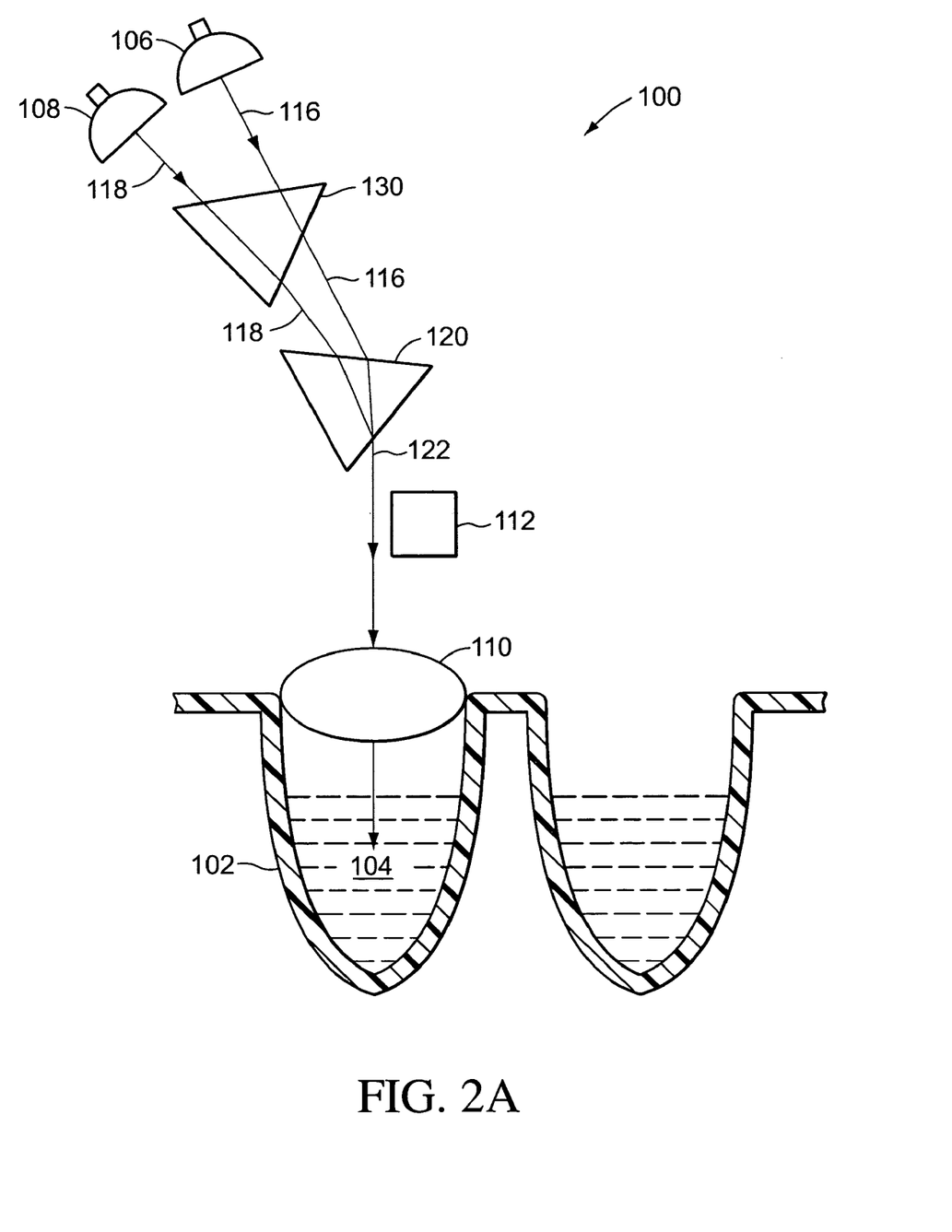
FIGS. 2A–2B illustrate a side, partial cross-sectional view of a biological sample detection system including two prisms according to various embodiments of the present teachings.

In various embodiments, as illustrated in FIG. 2A, a luminescent detection system 100 can include a sample chamber 102 adapted to receive a biological sample 204 containing one or more fluorescent-light emitting components, for example, fluorescent dyes. The system 100 can include a first excitation light source 106, a second excitation light source 108, an optical assembly 110, and a detection assembly 112 for detecting luminescent light emitted from the biological sample 104.

The first and second excitation light sources 106, 108 can be spatially separated from one another. The first excitation light source 106 can be configured to provide a first beam of light 116, and the second excitation light source 108 can be configured to provide a second beam of light 118. The first and second light sources 106, 108 can provide non-parallel first and second light beams 116, 118. The first and second beams of light 116, 118 can have optical spectra that differ from one another. For example, the first and second beams of light 116, 118 can have substantially different wavelengths.

The luminescent detection system 100 can include one or more optical blenders such as, for example, a first prism 130 and a second prism 120. The first prism 130 can be positioned proximal to the light sources 106, 108 than the second prism 120, can be positioned proximal to the biological sample 104 and distal to the light sources 106 and 108.

The first prism 130 can be positioned in the path of the first and second light beams 116 and 118. The first prism 130 can then decrease the angle between the first and second light beams 116 and 118. By decreasing the angle between them, the first and second light beams 116 and 118 can be combined in stages with each optical blending component providing incremental blending up to the final optical blending component that provides the output of a composite beam. This incremental blending can provide flexibility in selecting components and determining their positions relative to the light sources. As shown in FIG. 2A, prism 120 completes the optical blending by outputting composite beam 122 and directing it toward biological sample 104.

Figure 2B:
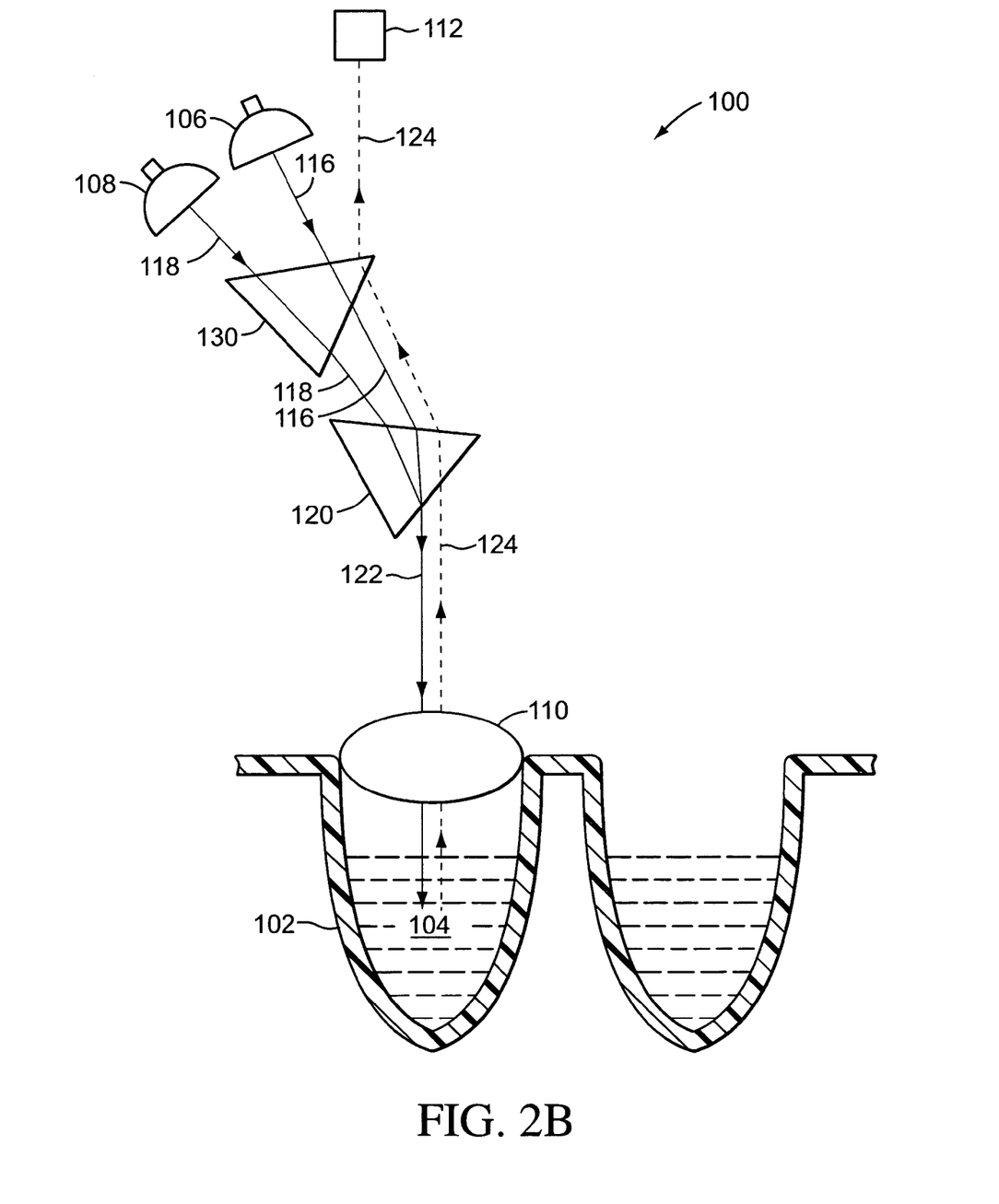

In various embodiments, as illustrated in FIG. 2B, the first prism 130 and second prism 120 can direct emission light 124 toward detector 112 unlike FIG. 2A where emission light 124 (not shown) does not pass through the prisms. In various embodiments, the luminescent detection system 100 shown in FIGS. 2A and 2B can include one or more additional light sources spatially separated and spectrally distinct from the first and second light sources 106 and 108. In various embodiments, a single prism 120 can be the optical blender.

Figure 3:
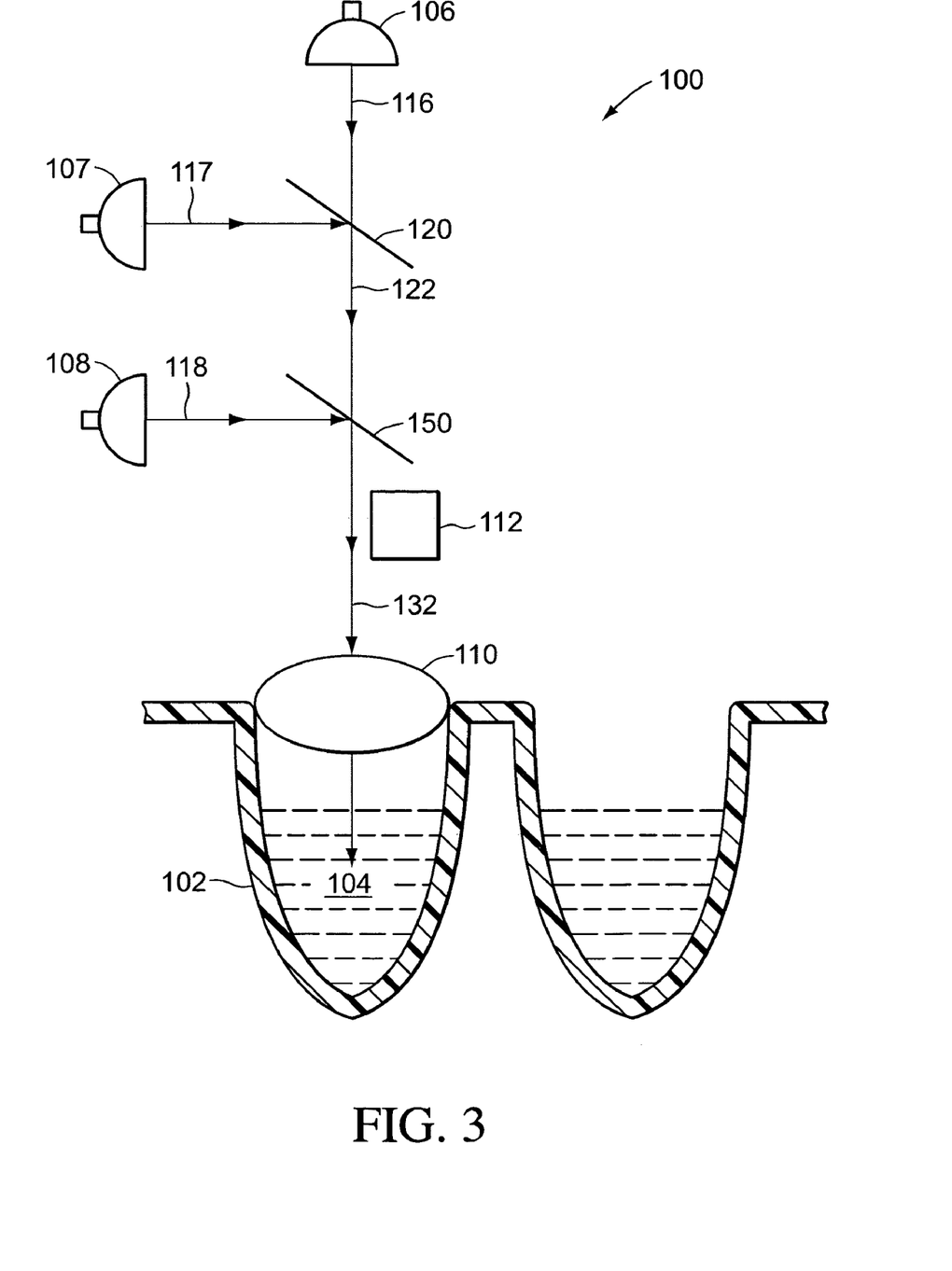
FIG. 3 illustrates a side, partial cross-sectional view of a biological sample detection system with two beamsplitters according to various embodiments of the present teachings.

In various embodiments, as illustrated in FIG. 3, a luminescent detection system 100 can include a third excitation light source 107, spatially separated from light sources 106 and 108, providing a third excitation beam 117 with a third optical spectrum, spectrally distinct from first and second excitation beams 116 and 118. The luminescent detection system 100 can include one or more optical blenders such as, for example, a first beam splitter 120 and a second beam splitter 150 as optical blenders. Beamsplitters, including dichroic, geometric, and 50—50, combine beams of light by substantially reflecting a first light beam and substantially transmitting a second light beam. The reflective/transmissive properties of beamsplitters can be based on wavelength differentiation or physical properties such as angle of incidence. Wavelength differentiation can be achieved by depositing thin-film interference coatings on either or both of the beamsplitter surfaces. The first beam splitter 120 can be positioned in the path of the first and third light beams 116 and 117. The first beam splitter 120 can be configured to combine the first and second light beams 116, 117 by transmitting the first light beam 116 and reflecting the second light beam 117, so as to output a first composite beam 122 of the combined first and second light beams 116, 117 directed toward the biological sample 104.

The second beam splitter 130 can be positioned in the path of the second light beam 118 and composite beam 122, which includes the combined first and second light beams 116, 117. The second beam splitter 150 can be configured to combine the first, second, and third light beams 116, 117, 118 by transmitting the first composite beam 122 and reflecting the second light beam 118. Thus, the second beam splitter 150 can output a second composite beam 132 of the combined first, second, and third light beams 116, 117, 118 directed toward biological sample 104. The optical assembly 110 can be between the second beam splitter 150 and the biological sample 104. In various embodiments, additional light sources that are spatially and spectrally distinct can be included in the luminescent detection system 100, as well as, additional beamsplitters. In various embodiments, beamsplitters can be collapsed into each other, for example, one beam splitter combining the first, second, and third beams of light 116, 117, 118.

In various embodiments, the detection assembly 112 can be configured to detect one or more particular wavelengths and, therefore, can detect luminescent light emitted by the biological sample having one of the detectable wavelengths. In various embodiments, the detection assembly 112 can include one or more detectors capable of detecting different emission light from different luminescent dyes in the biological sample 104. In embodiments having more than one detector, each detector can be set to receive a respective range of wavelengths of fluorescent light different than those of the other detector(s). In various embodiments, the detector assembly can include a plurality of detectors arranged as an array. In various embodiments, an array of transmission grating beam splitters can be provided to diffract the fluorescent light into a first contribution detectable by a first detector and a second contribution detectable by a second detector.

In various embodiments, the presence of various luminescent dyes in the biological sample 104 utilizing respective excitation wavelength ranges can be used to identify various nucleic acids in the sample 104. In various embodiments, the luminescent dyes can be fluorescent dyes chosen such that each dye possesses a discrete or substantially discrete optimum excitation wavelength range. In some embodiments, the emission wavelength ranges of various dyes can overlap. Each excitation light source can emit a respective wavelength range of light to cause fluorescence of a different fluorescent dye. The detection assembly 112 can be configured to detect the emission wavelengths of the various fluorescent dyes in the biological sample 104.

In various embodiments, the plurality of excitation light sources can provide excitation light selected respectively from the red, green, blue, violet, and/or ultra-violet spectra.

In various embodiments, the optical assembly 110 can include one or more lenses (not shown) configured to focus excitation light into the biological sample and/or collect and shape emission light emitted from the sample. Each of the lenses can be any lens known to practitioners in the art, for example, a Fresnel lens. The optical assembly 110 can include other devices known in the art arranged to direct, separate, filter, or focus the excitation light and/or emission light. For example, the optical assembly 110 can include a prism, a grating, or a mask. In various embodiments, the optical assembly 110 can include a prism in combination with a lens (not shown). In various embodiments, the optical assembly 110 can also include an excitation filter and/or an emission filter (not shown) as are know by practitioners in the art. In various embodiments, the optical assembly 110 can include an array of focusing lenses and/or an array of collimating lenses.

In various embodiments, the sample chamber 102 can be one well of a multi-well tray including a plurality of wells.

The optical assembly 110 and detection assembly 112 can form a unit that can be operatively aligned to direct excitation light toward the sample chamber 102 and/or direct emission light to the detection assembly 112 from the sample chamber 102. In various embodiments, a control device (not shown) can be provided to activate the unit.

In various embodiments, the optical assembly 110 can include a light pipe (not shown) to facilitate the direction of excitation light to a desired sample chamber 102 as is known by practitioners in the art. In various embodiments, crosstalk between the excitation light and fluorescent emission light from each sample chamber can be substantially reduced by using a mask (not shown), as is known by practitioners in the art. The mask can include a mask, masking elements, or a masking layer. In various embodiments, each sample chamber 102 can include a cover (not shown) on the well capable of operating as a collimating lens.

Figure 4A:
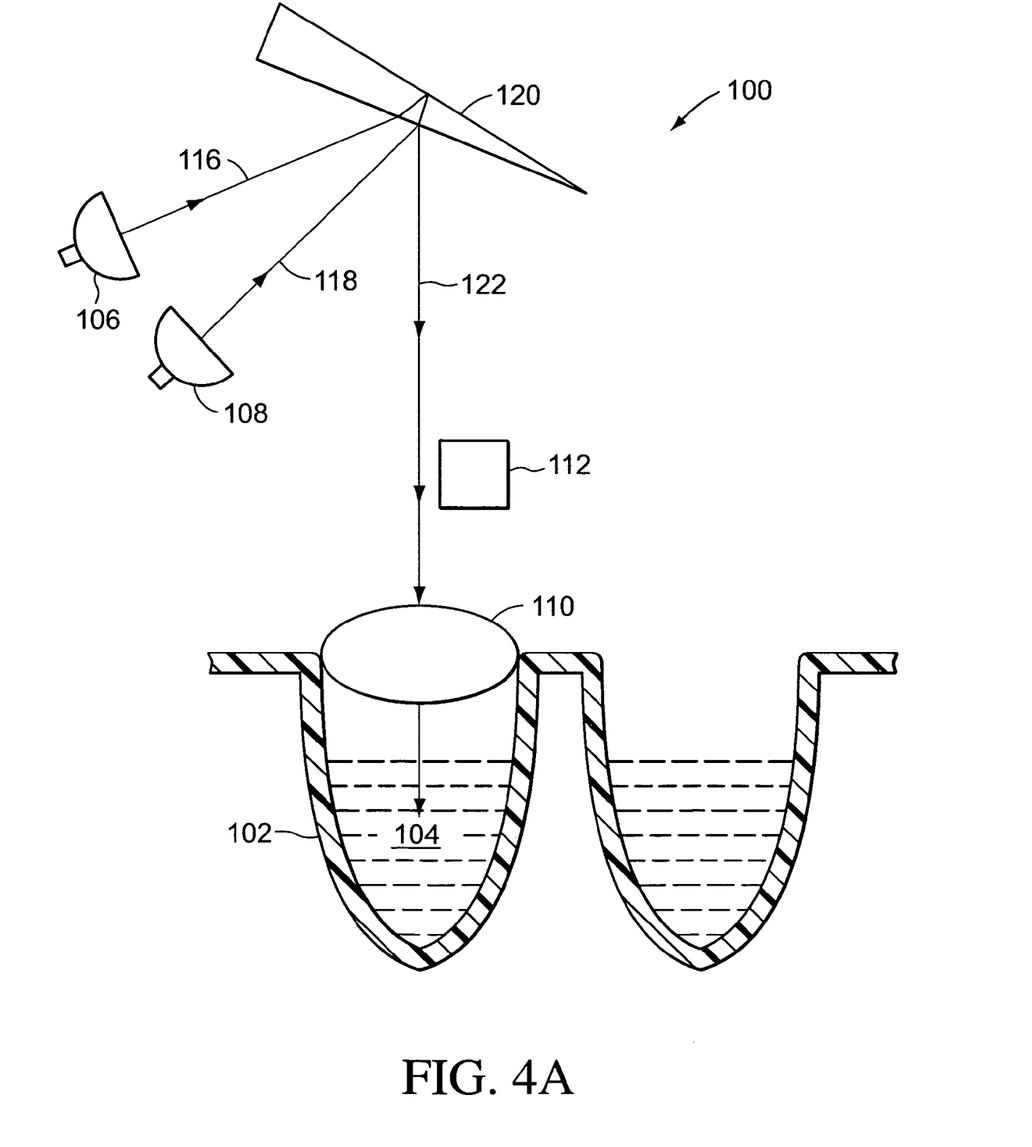
FIGS. 4A–4B illustrate a side, partial cross-sectional view of a biological sample detection system including a wedge according to various embodiments of the present teachings.
Figure 4B:
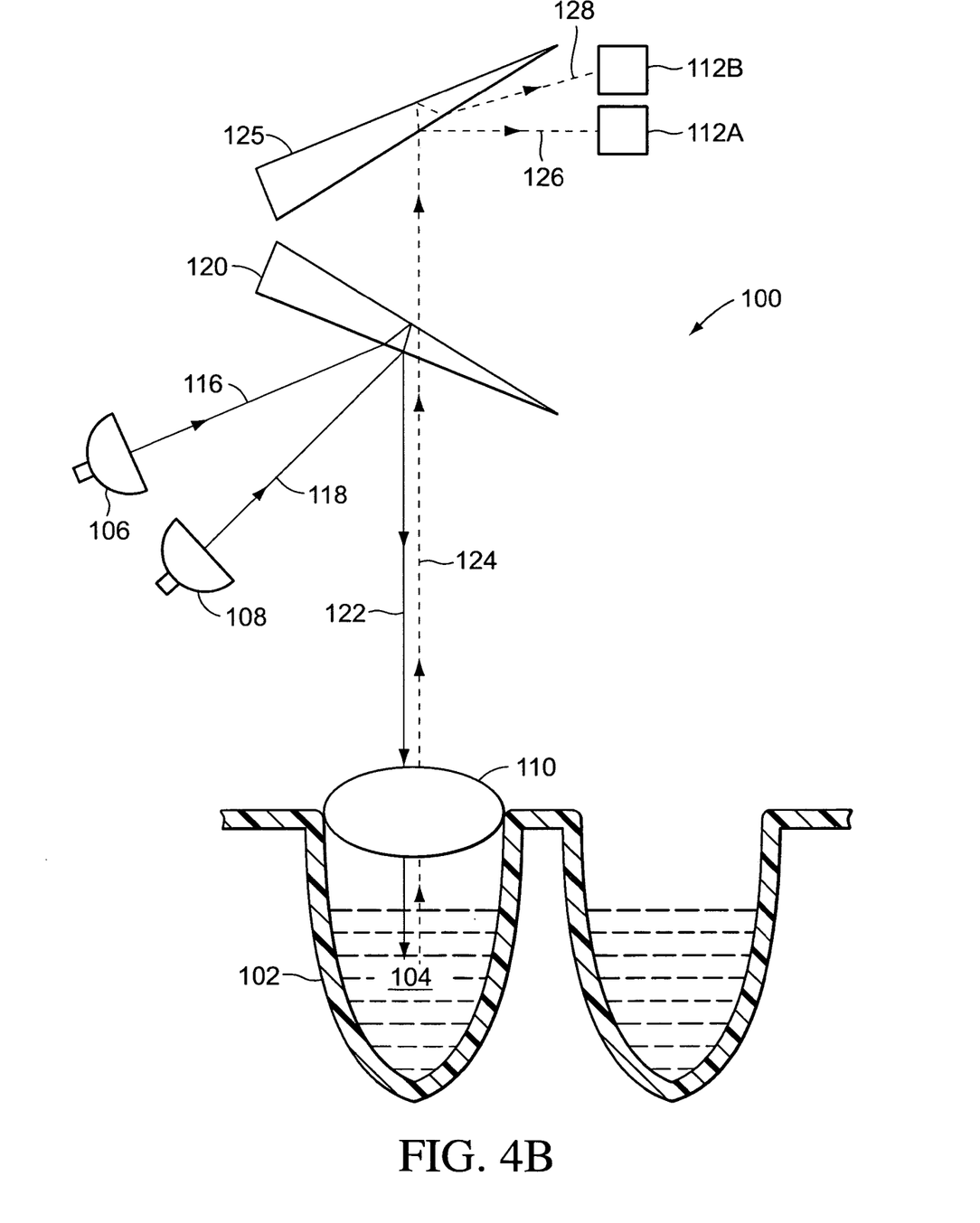

In various embodiments, as illustrated in FIGS. 4A and 4B, the optical blender can be a wedge, as described above. As illustrated in FIG. 4A, the wedge 120 can combine first beam 116 and second beam 118 into composite beam 122 by providing different light paths for each beam. As illustrated in FIG. 4B, a second wedge 125, in addition to first wedge 120, can separate emission light 124 into different contributions by different luminescent dyes in biological sample 104. As shown, a first contribution wavelength 126 can be directed to detector 112A and a second contribution wavelength 128 can be directed to detector 112B providing detection of each contribution by a detector configured to detect that contribution.

Figure 6A:
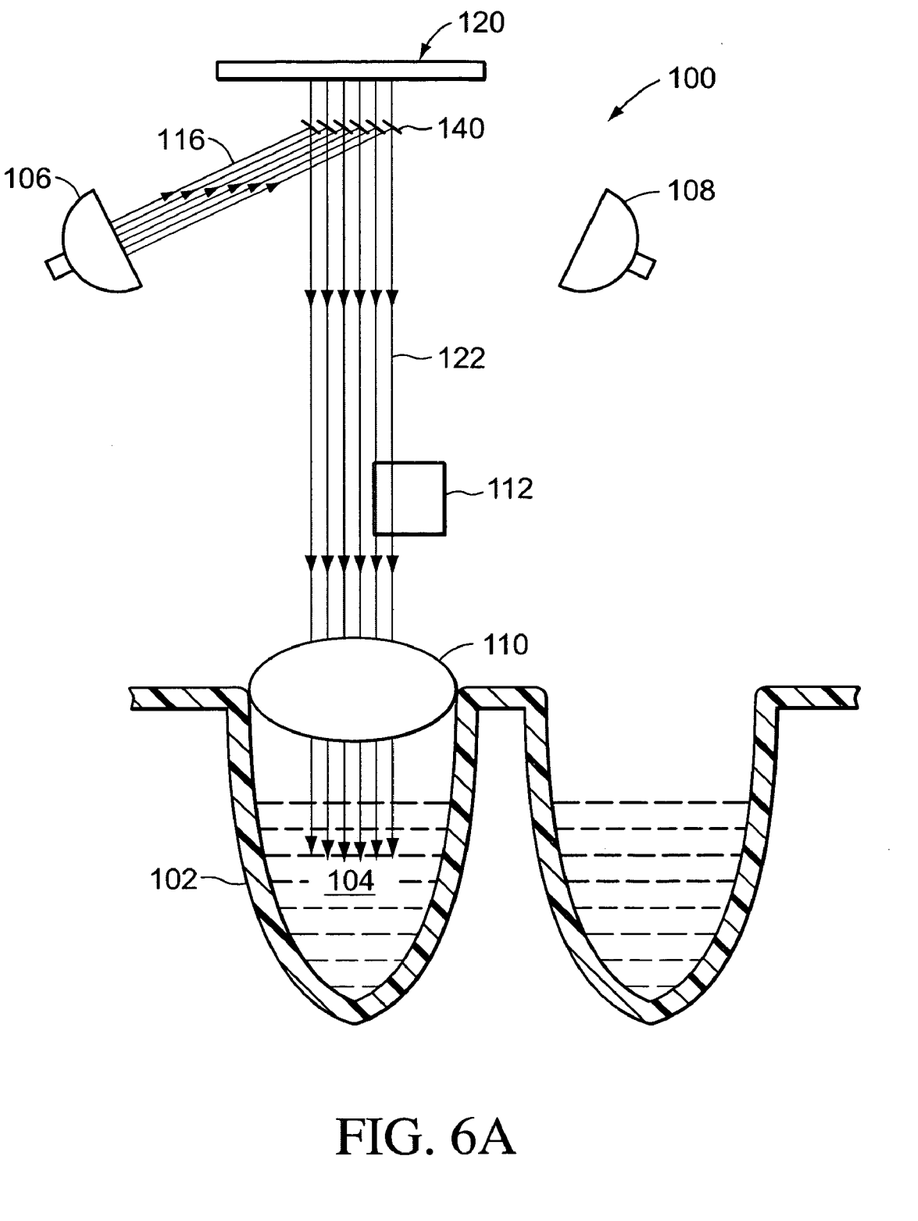
FIGS. 6A–6B illustrate a side, partial cross-sectional view of a biological sample detection system including a mirror array relay according to various embodiments of the present teachings.
Figure 6B:
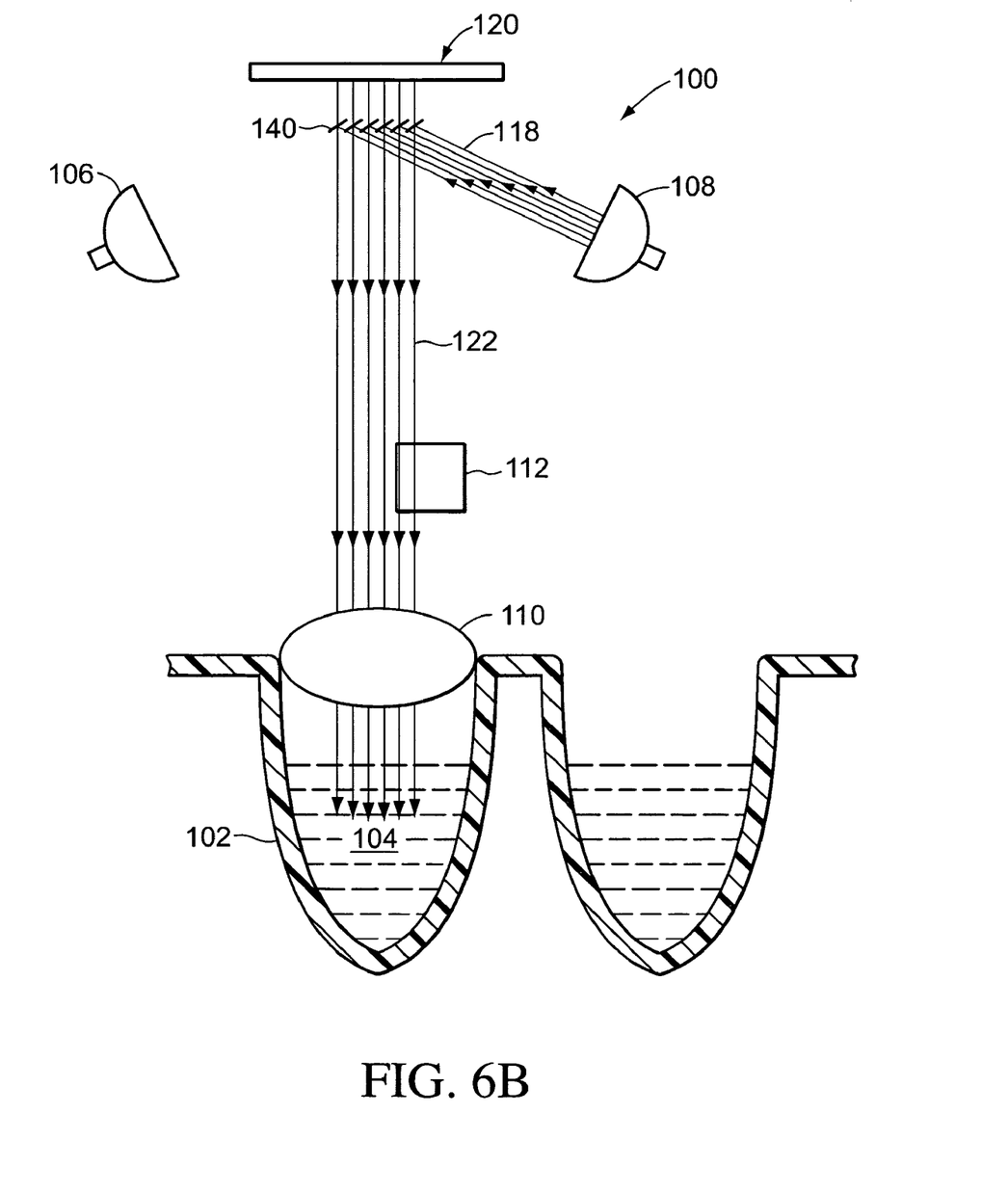

In various embodiments, as illustrated in FIGS. 6A and 6B, the optical blender can be a mirror array relay 120, for example, similar to those used in digital light projectors. The individually controllable mirrors 140 can be controlled by relay to physically blend first light beam 116 and second light beam 118. For illustrative purposes, FIGS. 6A and 6B show all mirrors 140 directed to a each light source 106 and 108, respectively, at one time. In operation, each mirror can be directed to any of the light sources to provide an output composite beam 122 directed toward the biological sample 104.

Figure 7A:
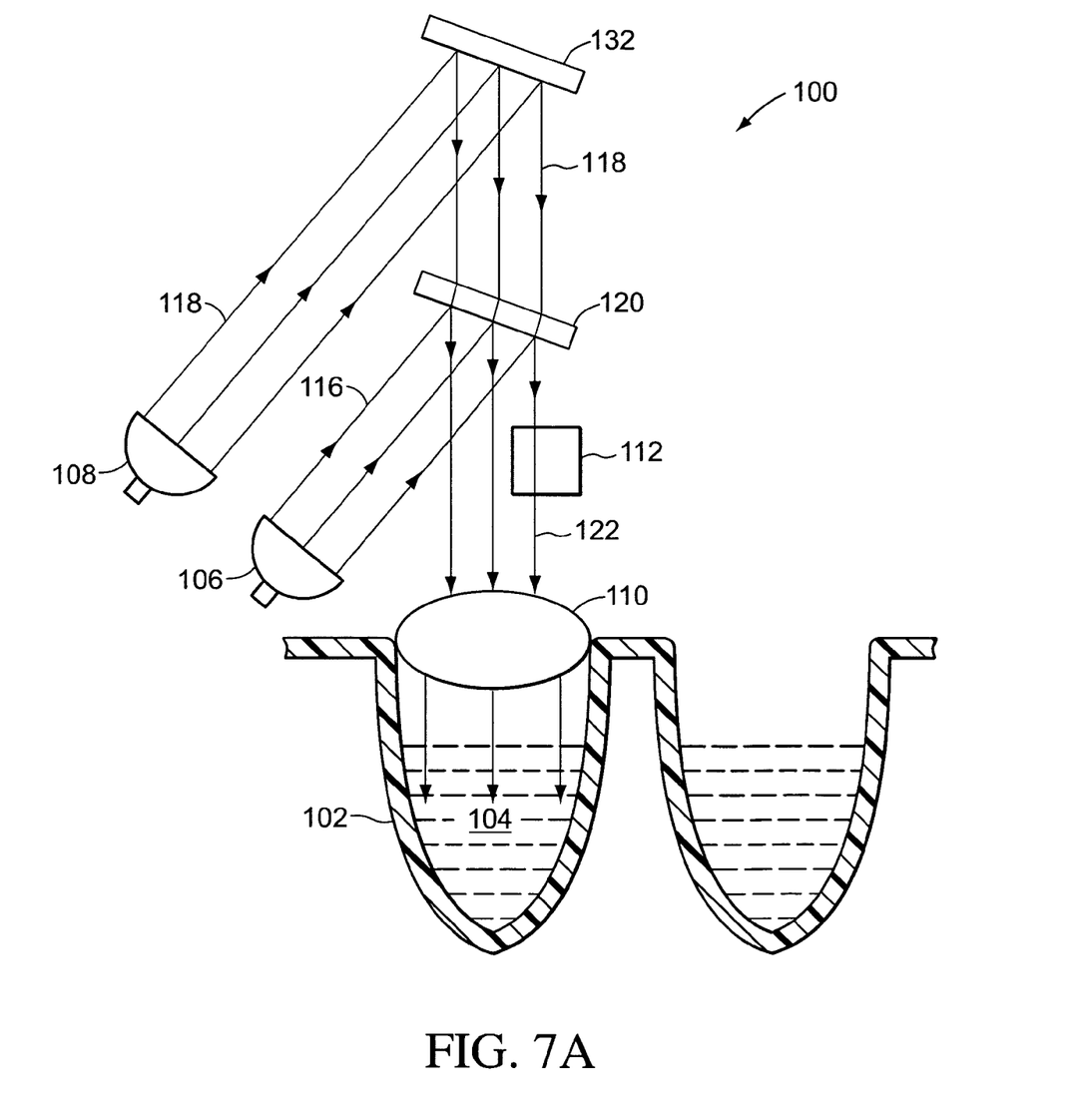
FIG. 7A–7B illustrate a side, partial cross-sectional view of a biological sample detection system including a mirror and beamsplitter according to various embodiments of the present teachings.
Figure 7B:
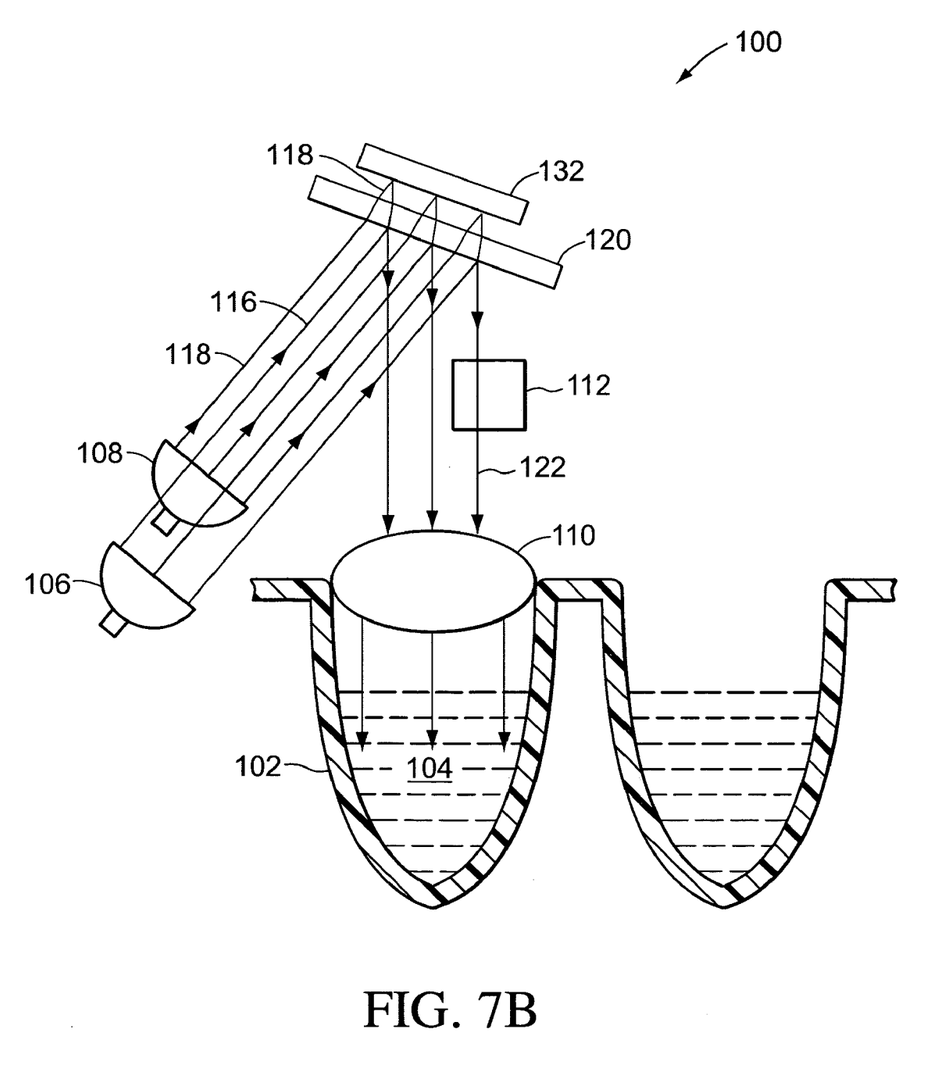

In various embodiments, as illustrated in FIGS. 7A and 7B, the first light beam 116 and second light beam 118 have parallel paths. First light source 106 and second light source 108 have spatially distinct locations and emit spectrally distinct spectra. Mirror 132 can reflect light beam 118 either directly from light source 108, as in FIG. 7A, or transmitted through beam splitter 120, as in FIG. 7B. Beam splitter 120 can transmit light beam 118 and reflect light beam 116 from light source 106. Beam splitter can combine the two light beams into composite beam 122 directed toward a luminescent dye that produces emission light in relation to nucleic acid present in the biological sample 104. In various embodiments, a third light beam from a third light source having a third optical spectrum, not shown in FIG. 7A or 7B, can be optically blended by the system. In such a system, mirror 132 can be replaced by a beam splitter that can reflect light beam 118 and can transmit the third light beam from the third light source. The third light source can be positioned on the opposite side of the beam splitter relative to the second light source 108.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "less than 10" includes any and all subranges between (and including) the minimum value of zero and the maximum value of 10, that is, any and all subranges having a minimum value of equal to or greater than zero and a maximum value of equal to or less than 10, e.g., 1 to 5.

It is noted that, as used in this specification and the appended claims, the singular forms "a," "an," and "the" include plural referents unless expressly and unequivocally limited to one referent. Thus, for example, reference to "a light source" includes two or more different light sources. As used herein, the term "include" and its grammatical variants are intended to be non-limiting, such that recitation of items in a list is not to the exclusion of other like items that can be substituted or added to the listed items.

Various embodiments of the teachings are described herein. The teachings are not limited to the specific embodiments described, but encompass equivalent features and methods as known to one of ordinary skill in the art. Other embodiments will be apparent to those skilled in the art from consideration of the present specification and practice of the teachings disclosed herein. It is intended that the present specification and examples be considered as exemplary only.

What is claimed is:

1. A biological sample excitation system, the system comprising:
    a first light source emitting a first light beam having a first optical spectrum;
    a second light source spatially separated from the first light source, the second light source emitting a second light beam having a second optical spectrum, wherein the second optical spectrum is different from the first optical spectrum, and wherein the first light beam and the second light beam have non-parallel paths; and
    an optical blender positioned in the paths of the first light beam and the second light beam, wherein the optical blender combines the first light beam and the second light beam into a composite beam directed toward a luminescent dye that produces emission light in relation to nucleic acid present in the biological sample,
    wherein the optical blender is a wedge, wherein the wedge comprises a dichroic surface and a reflective surface.

2. A biological sample excitation system, the system comprising:
    a first light source emitting a first light beam having a first optical spectrum;
    a second light source spatially separated from the first light source, the second light source emitting a second light beam having a second optical spectrum, wherein the second optical spectrum is different from the first optical spectrum, and wherein the first light beam and the second light beam have non-parallel paths; and
    an optical blender positioned in the paths of the first light beam and the second light beam, wherein the optical blender combines the first light beam arid the second light beam into a composite beam directed toward a luminescent dye that produces emission light in relation to nucleic acid present in the biological sample,
    wherein the optical blender comprises at least one of a diffraction grating, an optical prism, a beamsplitter, a wedge, and a mirror array relay, and
    wherein the optical blender comprises two or more optical blenders.

3. The biological sample excitation system of claim 2, wherein at least one of the optical blenders decreases an angle between the first light beam and the second light beam.

4. The biological sample excitation system of claim 2, wherein at least one of the optical blenders combines the composite beam with a third beam of light from a third light source spatially separated from the first light source and the second light source, wherein the third light source emits a third light beam having a third optical spectrum different from the first optical spectrum and the second optical spectrum.

5. The biological sample excitation system of claim 2, wherein the first source and the second light source comprise at least one of a laser, an electroluminescent light source, an chemiluminescent light source, an electrochemniluminescent light source, an incandescent light source, a fluorescent light source, an arc lamp, and a light emitting diode.

6. The biological sample excitation system of claim 2, wherein the first light source and second light source are light emitting diodes.

7. The biological sample excitation system of claim 2, wherein the optical blenders are beam splitters.

8. The biological sample excitation system of claim 2, further comprising a detector configured to detect the emission light generated in the biological sample.

9. The biological sample excitation system of claim 8, wherein the detector comprises two or more detectors.

10. The biological sample excitation system of claim 8, wherein the biological sample comprises multiple luminescent dyes with different emission light components, each dye excitable by at least one of the first light source, and the second light source.

11. The biological sample excitation system of claim 4, wherein the optical blenders are beam splitters.

12. The biological sample excitation system of claim 11, wherein the first light source, the second light source, and the third light source are light emitting diodes.

13. The biological sample excitation system of claim 12, further comprising a detector configured to detect the emission light generated in the biological sample.

14. The biological sample excitation system of claim 13, wherein the detector comprises two or more detectors.

15. The biological sample excitation system of claim 13, wherein the biological sample comprises multiple luminescent dyes with different emission light components, each dye excitable by at least one of the first light source, the second light source, and the third light source.

16. A biological sample detection system, the system comprising:
    a first light source emitting a first light beam having a first optical spectrum;
    a second light source spatially separated from the first light source, the second light source emitting a second light beam having a second optical spectrum, wherein the second optical spectrum is different from the first optical spectrum, and wherein the first light beam and the second light beam have non-parallel paths; and an optical blender positioned in the paths of the first light beam and the second light beam, wherein the optical blender combines the first light beam and the second light beam into a composite beam directed toward a luminescent dye that produces emission light in relation to nucleic acid present in the biological sample; and a detector configured to detect the emission light generated in the biological sample, wherein the detector comprises two or more detectors, and wherein the optical blender separates the emission light into two or more emission light components, and wherein each of the two or more detectors detects each of the two or more emission light components, wherein each emission light component is generated by different dyes.

* * * * *